United States Patent
Nakano

(10) Patent No.: US 7,587,576 B2
(45) Date of Patent: Sep. 8, 2009

(54) PARAMETER STORING METHOD, PARAMETER STORAGE DEVICE, MULTI-BODY PROBLEM PROCESSING APPARATUS, AND ADDRESS GENERATOR CIRCUIT

(75) Inventor: Youji Nakano, Minato-ku (JP)

(73) Assignee: NEC Corporation, Tokyo (JP)

( * ) Notice: Subject to any disclaimer, the term of this patent is extended or adjusted under 35 U.S.C. 154(b) by 463 days.

(21) Appl. No.: 11/580,896

(22) Filed: Oct. 16, 2006

(65) Prior Publication Data

US 2007/0094653 A1    Apr. 26, 2007

(30) Foreign Application Priority Data

Oct. 21, 2005    (JP) .............................. 2005-307209

(51) Int. Cl.
*G06F 12/00* (2006.01)
*G06F 19/00* (2006.01)

(52) U.S. Cl. ..................................................... 711/217

(58) Field of Classification Search ........................ None
See application file for complete search history.

(56) References Cited

U.S. PATENT DOCUMENTS

| 6,886,128 | B2 * | 4/2005 | Kuwazoe et al. ............ 714/792 |
| 7,003,717 | B2 * | 2/2006 | Kuwazoe et al. ............ 714/792 |
| 2002/0078419 | A1 * | 6/2002 | Kuwazoe et al. ............ 714/792 |
| 2005/0157824 | A1 * | 7/2005 | Kuwazoe et al. ............ 375/341 |

FOREIGN PATENT DOCUMENTS

| JP | 61128367 A | 6/1986 |
| JP | 4-77853 A | 3/1992 |
| JP | 5-89157 A | 4/1993 |
| JP | 05191923 A | 7/1993 |
| JP | 05282159 A | 10/1993 |
| JP | 6-223052 A | 8/1994 |
| JP | 06231114 A | 8/1994 |
| JP | 06231115 A | 8/1994 |
| JP | 9-251449 A | 9/1997 |

* cited by examiner

*Primary Examiner*—Kevin Verbrugge
(74) *Attorney, Agent, or Firm*—Sughrue Mion, PLLC

(57) ABSTRACT

The object of the present invention is the reduction of memory capacity in a multi-body problem processing apparatus. In a parameter storing method in multi-body problem processing for performing a molecular dynamics calculation for a plurality of particles existing in a three-dimensional space, parameters required to calculate a nonassociative force acting between particles subjected to the calculation are stored in a storage device and correspond to a combination of the particles subjected to the calculation.

4 Claims, 5 Drawing Sheets

| $P_i$ | $P_j$ | ADDRESS |
|---|---|---|
| 0 | 0 | 0 |
| : | : | : |
| 0 | N | N |
| 1 | 0 | N + 1 |
| : | : | : |
| 1 | N | 2N |
| 2 | 0 | 2N + 1 |
| : | : | : |
| 2 | N | 3N |
| 3 | 0 | 3N + 1 |
| : | : | : |
| 3 | N | 4N |
| 4 | 0 | 4N + 1 |
| : | : | : |
| : | : | : |
| N | N | $(N + 1)^2 - 1$ |

PARAMETER STORING METHOD, PARAMETER STORAGE DEVICE, MULTI-BODY PROBLEM PROCESSING APPARATUS, AND ADDRESS GENERATOR CIRCUIT

BACKGROUND OF THE INVENTION

1. Field of the Invention

The present invention relates to a multi-body problem processing apparatus for performing calculations for molecular dynamics, and more particularly, to a parameter storing method, a parameter storing device, a multi-body problem processing apparatus, and an address generator circuit which are suitable for performing the calculations.

2. Description of the Related Art

In multi-body problem processing apparatuses for performing calculations for molecular dynamics as disclosed in JP-A-6-223052 and JP-A-9-251449, a distance and an energy parameter must be taken into consideration in calculating nonassociative forces which act between multiple particles that exist within a three-dimensional space.

Conventionally, these parameters have been previously stored in a memory, such that parameters required for calculations are read to calculate the nonassociative force which acts between respective particles. Since these parameters differ depending on the type of particles, a number of parameters equal to the number of combinations of respective particles must be stored in the memory.

FIG. 1 is a block diagram illustrating the configuration of a main portion of a conventional multi-body problem processing apparatus. In the description of the prior art example, number P, which takes a value of 0 to N−1, is given in order to identify N types of particle species, and particle numbers in combination are designated by $P_i$ and $P_j$.

In FIG. 1, address generator circuit 101 stores addresses corresponding to particle numbers $P_i$, $P_j$, and storage device 103 stores parameters corresponding to the addresses.

Upon application of particle numbers $P_i$, $P_j$, address generator circuit 101 generates address S101 corresponding to particle numbers $P_i$, $P_j$, and outputs address S101 to processing unit 2. Processing unit 102 reads parameters stored in storage device 103 corresponding to address S101, and performs processing to provide processing result S102.

FIG. 2 is a table showing how addresses are stored in address generator circuit 101.

There are N types in each of the two particles (labeled particle numbers $P_i$, $P_j$) intended for calculation, with zero inclusive, so that the final value of the address is represented by $(N+1)^2-1$, and $(N+1)^2$ different addresses are generated in total. Storage device 103 for storing parameters corresponding to each address stores $(N+1)^2$ parameters corresponding to $(N+1)^2$ addresses.

While parameters required to perform calculations for molecular dynamics have been previously stored in a memory and are read as required for calculations to calculate nonassociative forces which act between respective particles, these parameters differ depending on the type of the particles, so that a number of parameters equal to the number of combinations of the respective particles must be stored in memory, causing an increase in memory capacity by a significant factor in memory capacity (gate amount).

SUMMARY OF THE INVENTION

The present invention has been made in view of the problems experienced by the prior art described above, and it is an object of the invention to provide a parameter storing method, a parameter storage device, a multi-body problem processing apparatus, and an address generator circuit, which are capable of reducing the memory capacity.

A parameter storing method according to the present invention is directed to multi-body problem processing for performing a calculation of molecular dynamics for a plurality of particles existing in three-dimensional space, wherein parameters required to calculate a nonassociative force acting between particles subjected to the calculation are stored in a storage device and which correspond to a combination of the particles subjected to the calculation.

A parameter storage device according to the present invention is for use in a multi-body problem processing apparatus for performing a calculation of molecular dynamics for a plurality of particles existing in a three-dimensional space, wherein the parameter storage device stores parameters required to calculate a nonassociative force acting between particles subjected to the calculation in correspondence to a combination of the particles subjected to the calculation.

A parameter storing method according to the present invention is directed to multi-body problem processing for performing a calculation of molecular dynamics for a plurality of particles existing in three-dimensional space. The method comprises the steps of:

storing parameters required to calculate a nonassociative force acting between particles subjected to the calculation in a storage device in correspondence to a combination of the particles subjected to the calculation;

generating an address signal indicative of a combination state of two particles subjected to the calculation; and upon receipt of the address signal, reading parameters stored in the storage device in correspondence to the address signal for performing processing.

A multi-body problem processing apparatus according to the present invention is configured to perform a calculation of molecular dynamics for a plurality of particles existing in three-dimensional space. The apparatus comprises:

a storage device for storing parameters required to calculate a nonassociative force acting between particles subjected to the calculation in correspondence to a combination of the particles subjected to the calculation;

an address generator circuit for generating an address signal indicative of a combination state of two particles subjected to the calculation; and a processing unit responsive to the address signal for reading parameters stored in the storage device which correspond to the address signal for performing processing.

In the multi-body problem processing apparatus described above, the address generator circuit may comprise:

a first and a second sector for receiving a first and a second particle number indicative of two particles subjected to the calculation, respectively;

a comparator circuit for comparing the first and second particle numbers in magnitude, and causing the first selector to select a larger particle number and the second selector to select a smaller particle number;

a first adder for subtracting one particle number from an output of the first selector;

a multiplier for multiplying the output of the first selector by an output of the first adder;

a ½ circuit for reducing the value produced by the multiplier to one half; and a second adder for adding an output of the ½ circuit and an output of the second selector.

The address generator circuit may further comprise:

a third selector for receiving the output of the first selector and "0"; and a detector circuit for comparing the output of the second selector with "0" and causing the third selector to select "0" when the output of the second selector is "0".

An address generator circuit according to the present invention is for use in a multi-body problem processing apparatus. The address generator circuit comprises:

a first and a second sector for receiving a first and a second particle number indicative of two particles subjected to the calculation, respectively;

a comparator circuit for comparing the first and second particle numbers in magnitude, and causing the first selector to select a larger particle number and the second selector to select a smaller particle number;

a first adder for subtracting one particle number from an output of the first selector;

a multiplier for multiplying the output of the first selector by an output of the first adder;

a ½ circuit for reducing the value produced by the multiplier to one half; and a second adder for adding an output of the ½ circuit and an output of the second selector.

The address generator circuit may further comprise:

a third selector for receiving the output of the first selector and "0"; and a detector circuit for comparing the output of the second selector with "0" and causing the third selector to select "0" when the output of the second selector is "0."

The molecular dynamics calculation requires a number of distance and energy parameters which is equal to the number of combinations of particle species, and the values of these parameters remain unchanged even when there is a change of places between particles in a combination. As previously shown in FIG. 2, addresses have been generated for a particular particle in order to calculate nonassociative forces between that particle and all remaining particles. For example, different addresses have been generated for a combination of particle numbers 3, 4 and a combination of particle numbers 4, 3, but the same parameters are stored in a storage device at these addresses.

The present invention takes advantage of the fact that parameters remain unchanged even when there is a change of places between particles in a combination. Specifically, a combination of serial numbers is given to a combination of particles subjected to the calculation, such that the address generator circuit uses the serial numbers to generate a memory address at which required parameters are stored. The address generator circuit generates the same memory address even when the serial numbers are interchanged within the combination. Consequently, data at the same memory address can be referenced even if the particles are interchanged.

The feature of the present invention can be used to reduce the number of stored parameters to one half, i.e., accomplish a significant reduction in memory capacity, thus resulting in a smaller gate amount, lower power consumption, and a smaller amount of generated heat.

DETAILED DESCRIPTION OF THE PREFERRED EMBODIMENTS

Next, embodiments of the present invention will be described.

Figure 3:
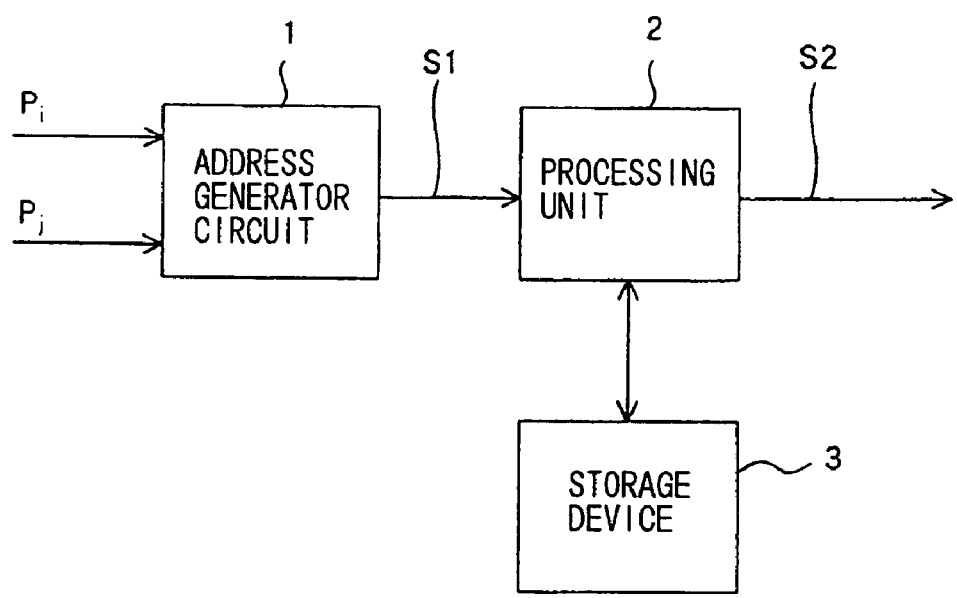
FIG. 3 is a block diagram illustrating the configuration of a main portion of a multi-body problem processing apparatus according to the present invention.

FIG. 3 is a block diagram illustrating the configuration of a main portion of a multi-body problem processing apparatus according to one embodiment of the present invention. In the description of this embodiment, number P, which takes a value of 0 to N−1, is given in order to identify N types of particle species, and particle numbers in combination are designated by $P_i$ and $P_j$.

As illustrated in FIG. 3, this embodiment comprises address generator circuit 1, processing unit 2, and storage device 3. Address generator circuit 1 stores addresses corresponding to particle numbers $P_i$, $P_j$, while storage device 3 stores parameters corresponding to addresses.

Figure 4:
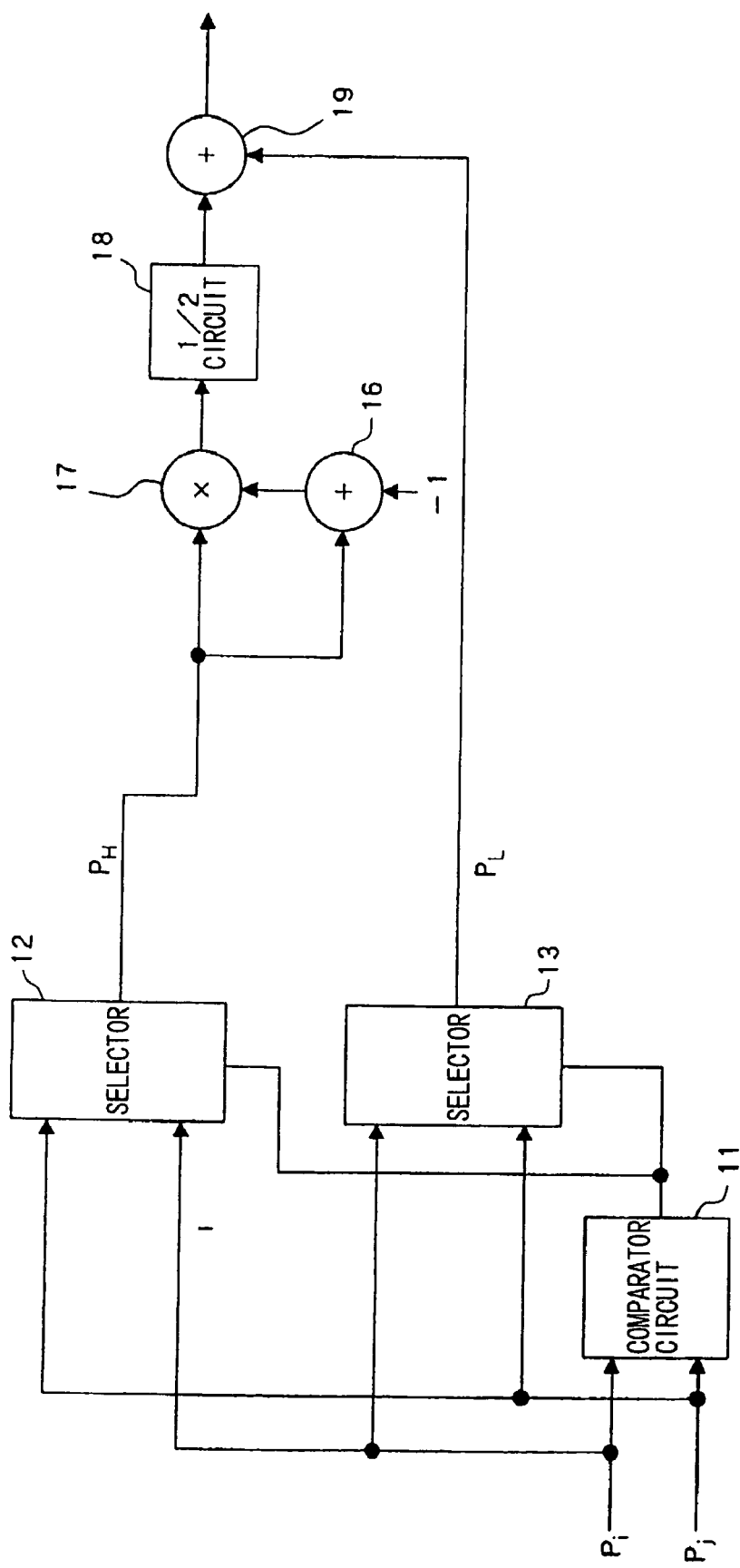
FIG. 4 is a circuit diagram illustrating the configuration of address generator circuit 1 in FIG. 3.

FIG. 4 is a circuit diagram illustrating the configuration of address generator circuit 1 in FIG. 3. In the following, the generation of an address in this embodiment will be described in detail with reference to FIG. 4.

Address generator circuit 1 comprises comparator circuit 11, selectors 12, 13, adder 16, multiplier 17, ½ circuit 18, and adder 19.

Particle numbers $P_i$, $P_j$ are applied to comparator circuit 11 and selectors 12, 13. Comparator circuit 11 compares particle numbers $P_i$, $P_j$ with each other, and causes selector 12 to select a larger particle number ($P_H$), and selector 13 to select a smaller particle number ($P_L$).

Larger particle number $P_H$ is multiplied by a value calculated by subtracting one particle number from particle number $P_H$ by adder 16 in multiplier 17, and the resulting number is reduced to one half by ½ circuit 18. Subsequently, the output of ½ circuit 18 is added to smaller particle number $P_L$ in adder 19 to generate an address.

Adder 16 and multiplier 17 calculate $P_H(P_H-1)$, where this calculation always results in an even number without fail, so that ½ circuit 18 may ignore the least significant bit. Finally, adder 9 adds $P_L$ delivered from selector 3 to the output of ½ circuit 18 to generate an address represented by the following equation:

$$\text{Address} = P_H(P_H-1)/2 + P_L$$

Figure 5:
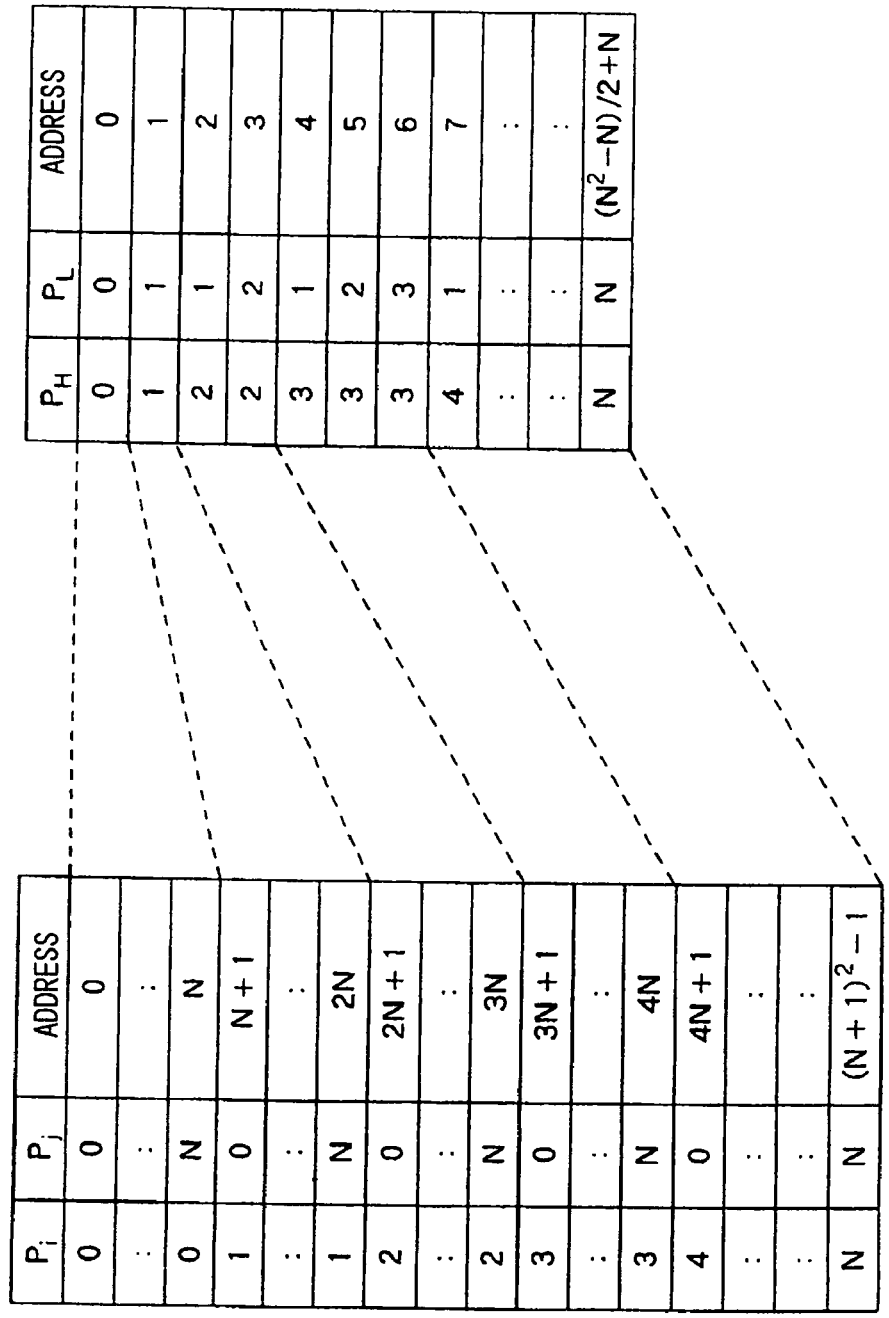
FIG. 5 is a table showing how addresses are generated by address generator circuit 1.

FIG. 5 is a table showing how addresses are generated by address generator circuit 1. Address generator circuit 101 shown in FIG. 2 generates $(N+1)^2$ different addresses corresponding to combinations of particle numbers $P_i$, $P_j$, as shown on the left-handed table, whereas this embodiment generates addresses each corresponding to a combination of larger particle number $P_H$ with smaller particle number $P_L$, that results from a comparison in magnitude between particle numbers $P_i$, $P_j$, as shown in the right-handed table. The addresses are generated by taking into account the fact that the same combination of particle species would result in the same parameters that are needed to calculate a nonassociative force therebetween. As a result, the number of combinations of particle numbers, for which addresses are generated, are approximately one half as much as the prior art example shown in FIG. 2.

Upon receipt of particle numbers $P_i$, $P_j$, address generator circuit 1 generates address S1 corresponding to particle numbers $P_i$, $P_j$, and outputs the address S1 to processing unit 2. Processing unit 2 reads parameters stored in storage device 3 in correspondence to address S1, performs processing, and delivers processing result S2.

Figures 1, 2:
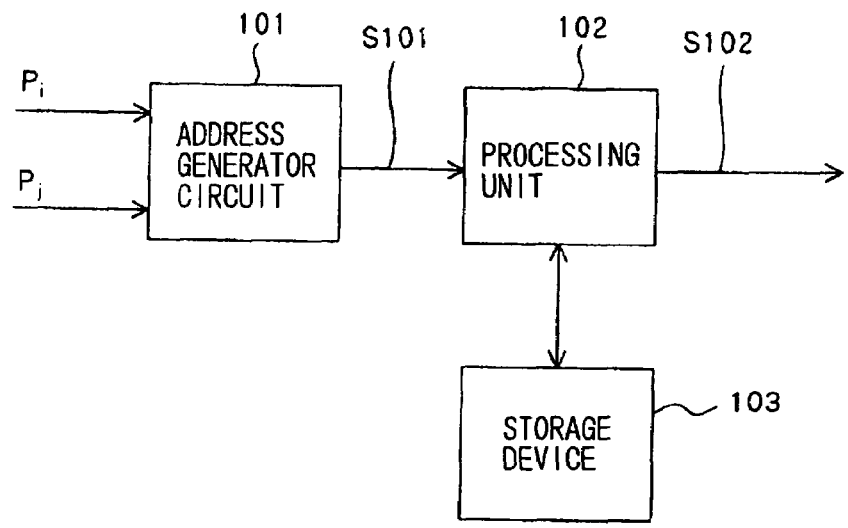
FIG. 1 is a block diagram illustrating the configuration of a main portion of a conventional multi-body problem processing apparatus.
FIG. 2 is a table showing how addresses are stored in address generator circuit 101.

The parameters stored in storage device 3 correspond to address S1 generated by address generator 1, where storage device 3 has a memory capacity approximately one half as much as that of storage device 103 shown in FIG. 1.

Figure 6:
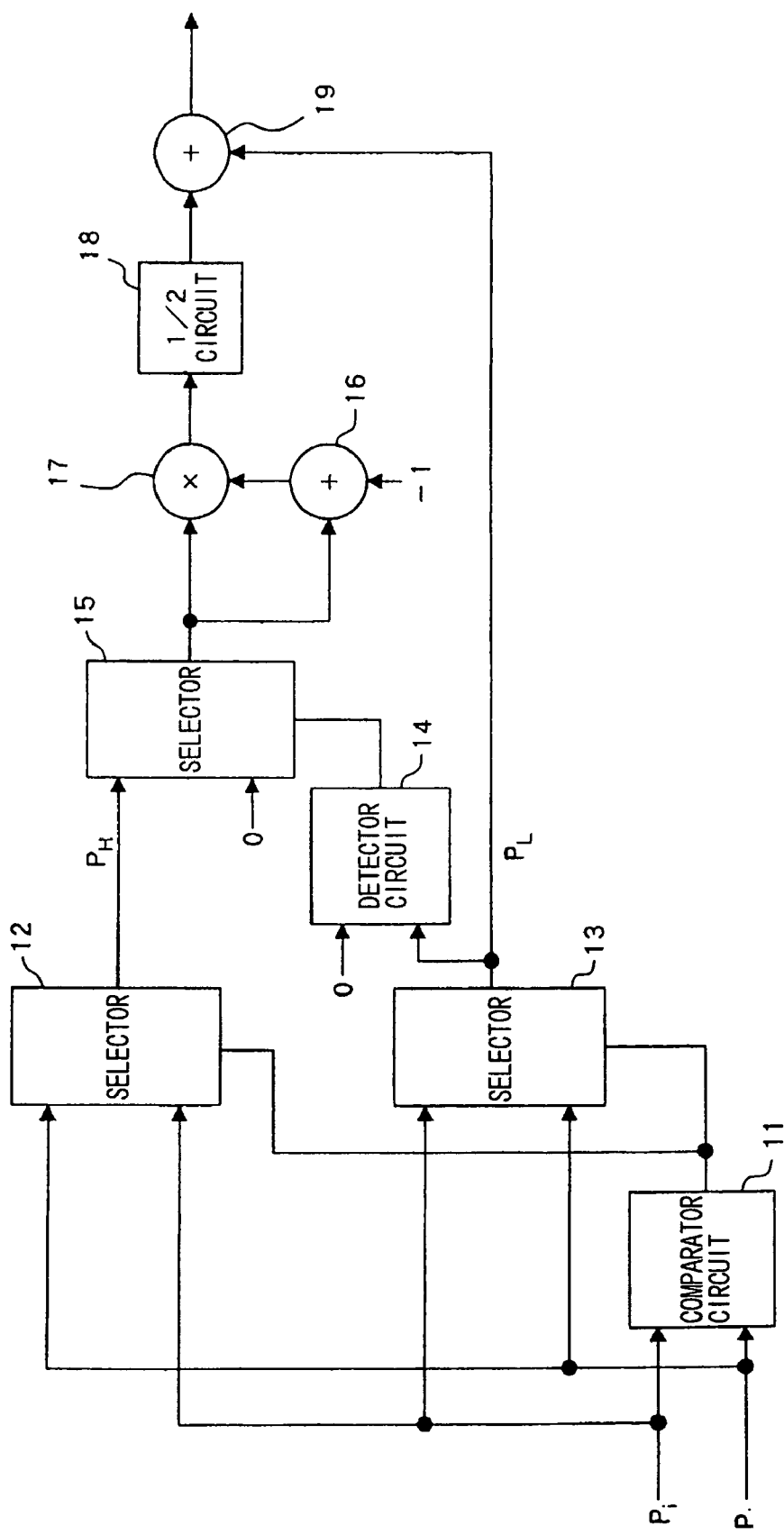
FIG. 6 is a circuit diagram illustrating the configuration of another embodiment of address generator circuit 1 in FIG. 3.

FIG. 6 is a circuit diagram illustrating the configuration of another embodiment of address generator circuit 1 in FIG. 3. In the following, the generation of an address in this embodiment will be described in detail with reference to FIG. 4.

Address generator circuit 1 in this embodiment additionally comprises detector circuit 14 and selector 15 in the configuration illustrated in FIG. 4. Detector circuit 14 receives smaller particle number $P_L$ delivered by selector 13 and "0" to detect whether or not smaller particle number $P_L$ is "0." Selector 15 receives larger particle number $P_H$ and "0" to select "0" when the result of the detection made by the detector circuit shows that smaller particle number $P_L$ is "0" and selects larger particle number $P_H$ when the result of the detection shows that smaller particle number $P_L$ is not "0".

In this embodiment, "0," which can be taken by particle numbers $P_i$, $P_j$, is delivered when no calculation is required to find a nonassociative force acting between particles. In a multi-body problem processing apparatus using this embodiment, a generated address is degenerated to "0" when at least one of the particle numbers $P_i$, $P_j$ in a combination has a particle number of "0."

What is claimed is:

1. A multi-body problem processing apparatus for performing a calculation of molecular dynamics for a plurality of particles existing in three-dimensional space, said apparatus comprising:
a storage device for storing parameters required to calculate a nonassociative force acting between particles subjected to the calculation and correspond to a combination of the particles subjected to the calculation;
an address generator circuit for generating an address signal indicative of a state in which two particles are combined and which are subjected to the calculation; and
a processing unit responsive to the address signal for reading parameters stored in said storage device and correspond to the address signal for performing processing, wherein said address generator circuit comprises:
a first and a second selector for receiving a first and a second particle number indicative of two particles subjected to the calculation, respectively;
a comparator circuit for comparing the magnitude of the first and second particle numbers, and causing said first selector to select a larger particle number and said second selector to select a smaller particle number;
a first adder for subtracting one particle number from an output of said first selector;
a multiplier for multiplying the output of said first selector by the output of said first adder;
a ½ circuit for reducing a value produced by said multiplier to one half; and
a second adder for adding an output of said ½ circuit and the output of said second selector.

2. The multi-body problem processing apparatus according to claim 1, wherein:
said address generator circuit comprises:
a third selector for receiving the output of said first selector and "0"; and
a detector circuit for comparing the output of said second selector with "0" and causing said third selector to select "0" when the output of said second selector is "0."

3. An address generator circuit for use in a multi-body problem processing apparatus, comprising:
a first and a second selector for receiving a first and a second particle number indicative of two particles subjected to the calculation, respectively;
a comparator circuit for comparing the magnitude of the first and second particle numbers, and causing said first selector to select a larger particle number and said second selector to select a smaller particle number;
a first adder for subtracting one particle number from an output of said first selector;
a multiplier for multiplying the output of said first selector by the output of said first adder;
a ½ circuit for reducing a value produced by said multiplier to half; and
a second adder for adding the output of said ½ circuit and the output of said second selector.

4. The address generator circuit according to claim 3, further comprising:
a third selector for receiving the output of said first selector and "0"; and
a detector circuit for comparing the output of said second selector with "0" and causing said third selector to select "0" when the output of said second selector is "0."

* * * * *